United States Patent [19]

Phillipps et al.

[11] Patent Number: 4,851,399
[45] Date of Patent: Jul. 25, 1989

[54] ISOQUINOLINE DERIVATIVES AND THEIR USE AS ANTI-CANCER AGENTS

[75] Inventors: Gordon H. Phillipps, Wembley; Paul S. Jones, Uxbridge; Martin E. Cooper, High Wycombe, all of United Kingdom

[73] Assignee: Glaxo Group Limited, London, United Kingdom

[21] Appl. No.: 78,716

[22] Filed: Jul. 28, 1987

[30] Foreign Application Priority Data

Jul. 29, 1986 [GB] United Kingdom ............... 8618398
May 5, 1987 [GB] United Kingdom ............... 8710608

[51] Int. Cl.$^4$ .................. A61K 31/395; C07D 221/18
[52] U.S. Cl. ..................................... 514/80; 514/283; 546/23; 546/42
[58] Field of Search ............... 546/23, 42; 514/283, 514/80

[56] References Cited

U.S. PATENT DOCUMENTS

| | | | |
|---|---|---|---|
| 3,336,317 | 8/1967 | Inman | 546/23 |
| 3,894,029 | 7/1975 | Winterfeldt | 546/23 |
| 4,029,659 | 6/1977 | Hannart | 546/23 |
| 4,033,966 | 7/1977 | Saura | 546/23 |
| 4,042,591 | 8/1977 | Kaul | 546/42 |
| 4,087,426 | 5/1978 | Shamma | 546/42 |
| 4,399,282 | 7/1980 | Miyasaka | 546/42 |
| 4,434,290 | 5/1981 | Bisagni | 546/42 |
| 4,444,776 | 11/1980 | Bisagni | 546/42 |

FOREIGN PATENT DOCUMENTS

| | | | |
|---|---|---|---|
| 108620 | 7/1975 | European Pat. Off. | 546/42 |
| 161102 | 6/1977 | European Pat. Off. | 546/42 |
| 2129799 | 7/1977 | United Kingdom | 546/42 |

OTHER PUBLICATIONS deKernion, J. B., "The Chemotheraphy of Advanced Bladder Carcinoma," Aug. 1971.
Smith, I. E., "Mitoxantrone (novantrone): A review : . ." Cancer Treatment Reviews (1983) 10, 103–155.
Stuart-Harris, R. C., "Mitoxantrone: An Active New Agent . . . " Cancer Chemother Parmacol (1984) 12:1–4.
Prestayko et al., CISPLATIN, Academic Press, 1980.
Cummings et al., "Phase I Study of 5-Fluorodeoxyrui-dine . . . ", Cancer Treatment Reports, vol. 63, No. 8, Aug. 1979, p. 1371.
CA, vol. 75, 143961y, (1971).
CA, vol. 77, 88260h, (1972).
CA, vol. 83, 152267u, (1975).
CA, vol. 83, 168484y, (1975).
CA, vol. 92, 75895d, (1980).
J. Heterocyclic Chem., vol. 15, pp. 1303–1307, (1978).
J. Organic Chemistry, vol. 37, No. 20, pp. 3111–3113, (1972).
"Reagents for Organic Synthesis" by Fieser et al., John Wiley & Sons, New York (1967), pp. 682–684.
Patent Abstracts of Japan, vol. 8, No. 130 (c-2290)[1567], 6-16-84.
"Synthesis and Reactions in the 1,2,3,4-Tetrahydroisoquinoline Series," C. R. Spray (1980), pp. 161–162, 193–194, 208–221 and 243 (PhD thesis).

Primary Examiner—Mary C. Lee
Assistant Examiner—J. Richter
Attorney, Agent, or Firm—Bacon & Thomas

[57] ABSTRACT

There are provided compounds of the general formula (1)

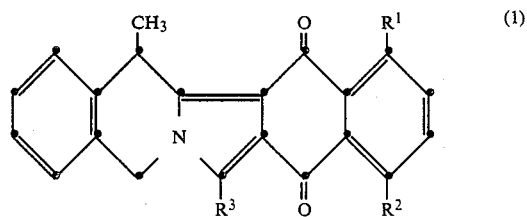

(wherein $R^1$ and $R^2$, which may be the same or different, each represents a hydrogen atom, a hydroxyl group or a group —OP(O) (OH) (OR$^4$) [where R$^4$ represents a hydrogen atom or an alkyl (optionally substituted by a hydroxyl, alkoxy, cyclic ether or cycloalkyl group), alkenyl cycloalkyl, aryl, aralkyl or aroylalkyl group], with the proviso that at least one of $R^1$ and $R^2$ represents a group —OP(O) (OH) (OR$^4$); and $R^3$ represents a hydrogen or halogen atom or a methyl group), and salts thereof. The novel compounds exhibit interesting anti-cancer activity.

12 Claims, No Drawings

ISOQUINOLINE DERIVATIVES AND THEIR USE AS ANTI-CANCER AGENTS

ISOQUINOLINE DERIVATIVES

This invention relates to new isoquinoline derivatives, to processes for their preparation, to pharmaceutical compositions containing them, and to their use in medicine.

Isoquinoline compounds have been reported in, for example, EP-A-108620 and EP-A-161102 as having anti-cancer activity. We have now found a novel group of isoquinoline compounds which have good anti-cancer activity. The novel compounds of the invention also exhibit particularly advantageous physico-chemical properties.

The invention thus provides compounds of the general formula (1)

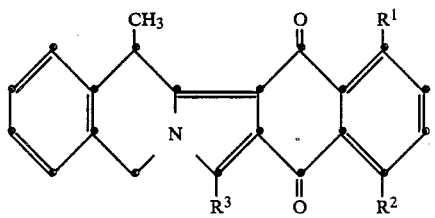

wherein
$R^1$ and $R^2$, which may be be same or different, each represents a hydrogen atom, a hydroxyl group or a group —OP(O)(OH)(OR$^4$) [where $R^4$ represents a hydrogen atom, or an alkyl (optionally substituted by a hydroxyl, alkoxy, cyclic ether or cycloalkyl group), alkenyl, cycloalkyl, aryl, aralkyl or aroylalkyl group], with the proviso that at least one of $R^1$ and $R^2$ represents a group —OP(O)(OH)(OR$^4$); and $R^3$ is a hydrogen or halogen atom or a methyl group; and salts, especially physiologically acceptable salts, thereof.

Compounds of formula (1) may exist as stereoisomers and/or tautomers and the invention is to be understood to include all such isomers of compounds of formula (1), including mixtures thereof.

Compounds of formula (1) may form salts with bases. It will be appreciated that, for pharmaceutical use, these salts should be physiologically acceptable, but other salts may find use, for example in the preparation of compounds of formula (1) as well as physiologically acceptable salts thereof. Examples of salts of compounds of general formula (1) include alkali metal salts such as lithium, sodium and potassium salts, amine salts, for example ammonium and mono-, di- or tri-substituted ammonium, e.g. triethylammonium salts and amino acid salts, for example arginine salts. Sodium salts are particularly useful.

References hereinafter to compounds of formula (1) and their use and preparation should, unless the context dictates otherwise, be taken to be references to the compounds and their salts, eg the physiologically acceptable salts.

In the compounds of formula (1), when the group $R^4$ is an alkyl group it may be for example a straight or branched $C_{1-8}$ alkyl group, or more especially a straight or branched $C_{1-6}$ alkyl group such as a methyl, ethyl, n-propyl, i-propyl, n-butyl or n-pentyl group. Such alkyl groups may be substituted by for example, a hydroxyl, $C_{1-4}$ alkoxy, eg methoxy or ethoxy, 3 to 7 membered cyclic ether eg tetrahydrofuranyl, or $C_{3-7}$ cycloalkyl eg cyclohexyl, groups.

When $R^4$ in the compounds of formula (1) represents an alkenyl group it may be for example a $C_{3-8}$ alkenyl group, eg allyl.

When $R^4$ in the compounds of formula (1) represents a cycloalkyl group it may be for example a $C_{3-7}$ cycloalkyl group, eg cyclohexyl.

When $R^4$ in compounds of formula (1) represents an aryl group it may be for example a phenyl group optionally substituted by a group $R^5$ where $R^5$ is a hydroxy, $C_{1-4}$ alkoxy, eg methoxy, or nitro group.

When $R^4$ is an aralkyl group it may be for example a phen$C_{1-3}$alkyl group in which the phenyl portion is optionally substituted by a group $R^5$ as just defined, and may be in particular a benzyl group.

When $R^4$ in the compounds of formula (1) represents an aroylalkyl group it may be for example a benzoyl $C_{1-3}$ alkyl group in which the benzoyl portion is optionally substituted in the phenyl ring by a group $R^5$ as defined above, and may be in particular a benzoylmethyl group.

When the group $R^3$ in the compounds of formula (1) is a halogen atom it may be a fluorine, chlorine, bromine or iodine atom.

According to one embodiment the invention provides compounds according to formula (1) in which;
$R^1$ and $R^2$, which may be the same or different, each represents a hydrogen atom, a hydroxyl group or a group —OP(O)(OH)(OR$^4$) [where $R^4$ represents a hydrogen atom or an alkyl (optionally substituted by a hydroxyl, alkoxy or cycloalkyl group) aryl or aralkyl group], with the proviso that at least one of $R^1$ and $R^2$ represents a group —OP(O)(OH)(OR$^4$); and $R^3$ is a hydrogen or halogen atom or a methyl group, and salts thereof.

In the compounds of formula (1), $R^3$ is preferably a methyl group or, more particularly, a hydrogen atom.

Particular examples of the group $R^4$ include a hydrogen atom, a straight or branched $C_{1-5}$ alkyl group, a $C_{1-4}$ alkoxyethyl group (such as 2-methoxyethyl), a tetrahydrofuranylmethyl group (eg 2-tetrahydrofuranylmethyl), a $C_{5-7}$ cycloalkylmethyl group (eg cyclohexylmethyl), a $C_{3-6}$ alkenyl group (eg allyl), a $C_{5-7}$ cycloalkyl group (eg cyclohexyl), phenyl, phenyl $C_{1-3}$ alkyl (eg benzyl) in which the phenyl portion is optionally substituted by a nitro (eg p-nitro) group or a benzoyl $C_{1-3}$ alkyl group (eg benzoylmethyl).

In the compounds of formula (1), $R^4$ is preferably a straight $C_{1-5}$ alkyl group (eg methyl or n-propyl), a tetrahydrofuranylmethyl group, a phenyl $C_{1-3}$ alkyl group (eg benzyl) or a benzoyl $C_{1-3}$ alkyl group (eg benzoylmethyl).

Compounds of formula (1) in which $R^1$ is a hydrogen atom and $R^2$ is a group —OP(O)(OH)(OR$^4$) (where $R^4$ is as defined above, especially benzyl or benzoylmethyl) and salts thereof are preferred.

A preferred group of compounds of formula (1) are those in which $R^1$ is a hydrogen atom, $R^2$ is a group —OP(O)(OH)(OR$^4$) and $R^3$ is a hydrogen atom and salts thereof. Such compounds in which $R^4$ is a straight $C_{1-5}$ alkyl group (eg methyl or n propyl), a tetrahydrofuranylmethyl group, a phenyl $C_{1-3}$ alkyl group (eg benzyl) or a benzoyl$C_{1-3}$-alkyl group (eg benzoylmethyl) are particularly preferred.

A particularly important compound according to the invention is phenylmethyl, [5,8,13,14-tetrahydro-14- methyl-8,13-dioxobenz[5,6]-isoindolo[2,1-b]isoquinolin-9-yl]phosphoric acid and the salts thereof, particularly the sodium salt.

Another important compound according to the invention is 2-oxo-2-phenylethyl, [5,8,13,14-tetrahydro-14-methyl-8,13-dioxobenz[5,6]-isoindolo[2,1-b]isoquinolin-9-yl]phosphoric acid and the salts thereof, particularly the sodium salt.

The compounds of formula (1) possess anticancer activity, particularly against tumours such as carcinomas, sarcomas and hepatomas.

Thus, when a compound of formula (1) is administered intraperitoneally or intravenously to mice with a subcutaneous tumour arising from an implant of S180 cells, subsequent examination has shown that tumour growth has been significantly reduced and in some cases total regression of the tumour has occurred. Activities against HT29 Human Colon Xenograft in Nude Mice and Mouse Adenocarcinoma MAC30T have also been shown.

Compounds according to the invention also have especially favourable physico-chemical properties. Thus, for example, compounds of the invention have improved water solubility at near to physiological pH [e.g. pH 6.0 to pH 8.0] over the isoquinoline compounds described in EP-A-108620 and EP-A-161102 which makes them particularly suitable for formulation for parenteral administration.

According to a further aspect of the present invention we therefore provide a compound of formula (1) or a physiologically acceptable salt thereof for use in the treatment of the human or non-human animal body to combat cancer, particularly tumours, therein.

According to a yet further aspect of the present invention we provide the use of a compound of formula (1) or a physiologically acceptable salt thereof for the manufacture of a therapeutic agent for the treatment of the human or non-human animal body to combat cancer, particularly tumours, therein.

According to a still further aspect of the present invention we provide a method of treatment of the human or non-human animal body to combat cancers, particularly tumours, therein, which method comprises administering to the said body an effective amount of a compound of formula (1) or a physiologically acceptable salt thereof.

It will be appreciated that the compounds according to the invention may advantageously be used in conjunction with one or more other therapeutic agents, such as for example anti-emetic agents, immunosuppressive agents or different anti-cancer agents. It is to be understood that the present invention covers the use of a compound of formula (1) or a physiologically acceptable salt thereof in combination with one or more other therapeutic agents.

In a further aspect of the present invention we provide a pharmaceutical composition comprising as an active ingredient a compound of formula (1) or a physiologically acceptable salt thereof together with one or more pharmaceutical carriers or excipients.

The compounds according to the invention may be formulated for administration in any convenient way, and the invention therefore also includes within its scope pharmaceutical compositions comprising a compound of formula (1) or a physiologically acceptable salt thereof adapted for use in human or veterinary medicine. Such compositions may be presented for use in conventional manner in admixture with one or more physiologically acceptable carriers or excipients. The compositions may optionally further contain one or more other therapeutic agents such as a different anti-cancer agent or an anti-emetic agent or an immunosuppressive agent.

Thus, the compounds according to the invention may be formulated for oral, buccal, topical, rectal or, preferably, parenteral administration (eg by bolus injection or intravenous infusion).

Injections are sterile products and may be presented in unit dose form, for instance as ampoules, vials, small volume infusions or pre-filled syringes, or in multi-dose containers, for example, with an added preservative. The compositions may take such forms as solutions, suspensions or emulsions in aqueous or non-aqueous vehicles, and may contain formulatory agents such as anti-oxidants, buffers, bulking agents, chelating agents, antimicrobial agents, solubilising agents, surfactants and/or tonicity adjusting agents. Alternatively, the active ingredient (with our without added substances) may be in a dry form for constitution with a suitable vehicle, eg sterile pyrogen-free water or dextrose, before use. The dry solid presentation may be prepared by filling a sterile powder aseptically into individual sterile containers or by filling a sterile solution aseptically into each container and freeze-drying.

The compounds according to the invention may also be formulated as compositions for oral administration. As tablets or capsules, they may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, surfactants, non-aqueous vehicles, preservatives, sugars, sweetening agents, buffers, colours, antioxidants and/or flavours. The compounds may also be formulated as suppositories, eg containing conventional suppository bases such as cocoa butter or other glycerides.

For buccal administration from the compositions may take the form of tablets or lozenges formulated in conventional manner.

For topical administration the compounds according to the invention may be formulated as ointments, creams, lotions, powders, pessaries, sprays, aerosols or drops (eg eye or nose drops). Ointments and creams may, for example, be formulated with an aqueous or oily base with the addition of suitable thickening and/or gelling agents. Such bases may thus, for example, include water and/or an oil such as liquid paraffin or a vegetable oil such as arachis oil or castor oil. Lotions may be formulated with an aqueous or oily base and will in general also contain one or more emulsifying agents, stabilising agents, dispersing agents, suspending agents, thickening agents and/or colouring agents. Powders may be formed with the aid of any suitable powder base, for example talc, lactose or starch. Drops may be formulated with an aqueous or non-aqueous base also comprising one or more dispersing agents, solubilising agents or suspending agents. Aerosol sprays are conveniently delivered from pressurised packs, with the use of a suitable propellant, eg dichlorodifluromethane, trichlorofluoromethane, dichlorotetrafluoroethane, carbon dioxide or other suitable gas.

The compositions may contain 0.1–100% of the active material.

It may be possible to target a compound of the invention to a tumour by including in the composition specialised drug carrier systems such as liposomes, albumen microspheres or monoclonal antibodies.

For systemic administration the daily dosage as employed for adult human treatment will generally be within the range of from 5 mg to 5000 mg, preferably 50 mg to 2000 mg, which may be administered in 1 to 5 divided daily doses, for example, depending on the route of administration and the condition of the patient. When the compositions comprise dosage units, each unit will preferably contain 10 mg to 2000 mg of active ingredient, for example 50 mg to 1000 mg.

For topical administration the daily dosage as employed for adult human treatment will generally range from 0.1 mg to 1000 mg, depending on the condition of the patient.

The compounds useful according to the invention may be prepared by a number of processes described in the following, wherein the various groups and symbols are as defined for formula (1) unless otherwise specified.

Thus, according to one process (A) a compound of formula (1) may be prepared by reacting a compound of formula (2)

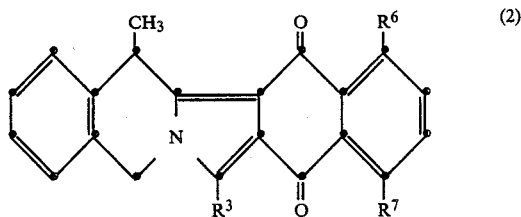

(2)

[in which one of $R^6$ and $R^7$ represents a group —OP(O)($X^1$)($X^2$) (where $X^1$ represents an atom or group convertable to a hydroxyl group and $X^2$ represents a hydroxyl group or an $X^1$ moiety) and the other represents a hydrogen atom, a hydroxyl group or a group —OP(O)($X^1$)($X^2$) as just defined] to convert at least one $X^1$ moiety to hydroxy to produce a compound of formula (1), for example by hydrolysis or ether cleavage.

Examples of $X^1$ as atoms capable of being converted to hydroxy include halogen atoms such as chlorine or bromine atoms.

Examples of $X^1$ as groups capable of being converted to hydroxy include the group $OX^3$ [where $X^3$ may be, for example, an alkyl group (optionally substituted by a hydroxyl, alkoxy, cyclic ether or cycloalkyl group) or an alkenyl, cycloalkyl, aryl, aralkyl or aroylalkyl group].

The conversion of $X^1$ to hydroxy may be carried out using conventional procedures. Thus, for example, a halogen atom may be displaced by a hydroxyl group by hydrolysis, eg basic hydrolysis using a suitable base such as an alkali metal hydroxide in a suitable solvent eg aqueous tetrahydrofuran.

The conversion of $OX^3$ to hydroxy may be carried out using a nucleophile eg a halide ion such as an iodide ion (obtained, for example, from an alkali metal halide such as sodium iodide) or a quaternary ammonium halide such as triethylamine hydroiodide in an inert solvent such as a ketone (eg acetone or butan-2-one) or a substituted amide (eg dimethylformamide), or by reaction with a trialkylsilyl iodide such as trimethylsilyl iodide in a solvent such as a halogenated hydrocarbon (eg carbon tetrachloride) followed by hydrolysis, eg basic hydrolysis using a suitable base such as an alkali metal hydroxide.

The reaction may be carried out at any suitable temperature, for example in the range −10° to +100° C.

It will be appreciated that in accordance with conventional practice the reaction may be managed such that when —OP(O)($X^1$)($X^2$) represents —OP(O)(O$X^3$)(O$X^3$) only one of the two $OX^3$ groups is converted to a hydroxyl group. In these circumstances secondary phosphates of formula (1) [ie in which $R^4$ is an alkyl group (optionally substituted by a hydroxyl, alkoxy, cyclic ether or cycloalkyl group) or an alkenyl, cycloalkyl, aryl, aralkyl or aroylalkyl group] are prepared. Alternatively, both $OX^3$ groups may be converted to hydroxyl groups using trimethylsilyl iodide. In these circumstances primary phosphates of formula (1) [i.e. in which $R^4$ is a hydrogen atom] are prepared.

It will be further appreciated that the reaction may be managed such that when an alkali metal halide (such as lithium, sodium or potassium iodide) is used the appropriate alkali metal salt of a compound of formula (1) is prepared.

According to another process (B) a compound of formula (1) may be prepared by reacting a compound of formula (3)

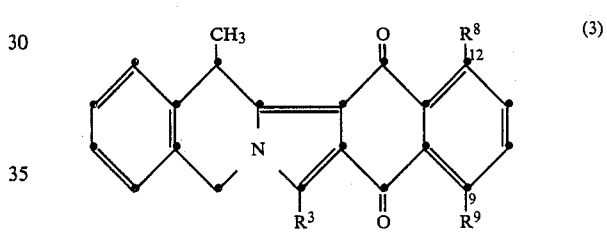

(3)

(in which one of $R^8$ and $R^9$ represents a hydroxyl group and the other represents a hydrogen atom or a hydroxyl group) to convert a hydroxyl group at the 9 and/or 12 position to a group —OP(O)(OH)(O$R^4$) where $R^4$ is as defined in formula (1) above.

The conversion may be effected by conventional means, for example by reaction of a compound of formula (3) with a halophosphate HalP(O)(OH)(O$R^4$) or HalP(O)($X^1$)($X^2$) (where Hal is a halogen atom eg chlorine and $X^1$ and $X^2$ are as previously defined) or a pyrophosphate ($R^4$O)(HO)(O)P—O—P(O)(OH)(O$R^4$) or ($X^1$)($X^2$)(O)P—O—P(O)($X^1$)($X^2$) (where $X^1$ and $X^2$ are as previously defined), followed, where necessary, by conversion of one or more $X^1$ moieties to hydroxy according to the procedure described in process (A) above. The reaction with the phosphorylating agent may conveniently be carried out in the presence of a base, for example an alkali metal hydride such as sodium hydride, or an alkali or alkaline earth metal carbonate eg potassium carbonate in an inert solvent such as an ether, e.g. tetrahydrofuran, an aromatic hydrocarbon eg toluene or a ketone eg acetone or a mixture of such solvents. The reaction may conveniently be carried out at a temperature in the range of 0° C. to 100° C. eg 20° C. It will be appreciated that reaction with a halophosphate HalP(O)($X^1$)($X^2$) or a pyrophosphate ($X^1$)($X^2$)(O)P—O—P(O)($X^1$)($X^2$) leads initially to the formation of a compound of formula (2) which may, if desired, be isolated.

According to another process (C) a compound of formula (1) in which $R^3$ is a hydrogen atom or a methyl group may be prepared by condensing a quinone of formula (4)

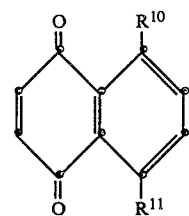
(4)

[in which one of $R^{10}$ and $R^{11}$ represents a group —OP(O)(OH)(OR$^4$) or —OP(O)(X$^1$)(X$^2$) (where X$^1$ and X$^2$ are as defined above) and the other represents a hydrogen atom, a hydroxyl group, a group —OP(O)(OH)(OR$^4$) or a group —OP(O)(X$^1$)(X$^2$) (where X$^1$ and X$^2$ are as defined above)] with a compound of formula (5)

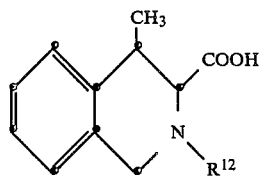
(5)

(in which $R^{12}$ represents a hydrogen atom or a group —CHO or —COCH$_3$) and subsequently, if required, converting one or more X$^1$ moieties to hydroxy to form a compound of formula (1).

The reaction between the compounds of formulae (4) and (5) may be carried out in the presence of an alkanoic acid anhydride, such as acetic anhydride, at an elevated temperature, eg 100° C. The conversion of one or more X$^1$ moieties to hydroxy may be effected using conditions described in process (A) above.

The compounds of formulae (1), (2) and (3) in which $R^3$ is a halogen atom may be prepared by halogenating a corresponding compound in which $R^3$ is a hydrogen atom. Standard halogenation procedures may be used, for example, by reaction with a N-chloro-, N-bromo- or N-iodoimide, eg N-chloro, N-bromo- or N-iodosuccinimide, or perchloryl fluoride in an inert solvent such as dichloromethane at ambient temperature.

The compounds of formula (2) may be prepared from compounds of formula (3) as described above in Process (B). Alternatively, the compounds of formula (2) in which $R^3$ is hydrogen or methyl may be prepared by condensing a compound of formula (4) in which one of $R^{10}$ and $R^{11}$ is a group —OP(O)(X$^1$)(X$^2$) and the other is a hydrogen atom, a hydroxyl group or a group —OP(O)(X$^1$)(X$^2$) with a compound of formula (5) according to the method of process (C) above.

The compounds of formula (3) in which $R^3$ is hydrogen or methyl may be prepared by condensing a quinone of formula (6)

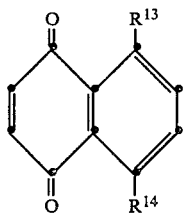
(6)

(in which one of $R^{13}$ and $R^{14}$ is a hydroxyl group or a protected hydroxyl group such as an acyloxy group eg acetoxy or halomethylcarbonyloxy and the other is a hydrogen atom, a hydroxyl group or a protected hydroxy group as just defined) with a compound of formula (5) according to the method of process (C) above, followed, where necessary, by removal of the protecting group, eg under acidic conditions using, for example, hydrochloric acid in a solvent such as tetrahydrofuran.

The compounds of formula (4) may be prepared by phosphorylation of a compound of formula (7)

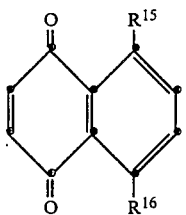
(7)

(in which one of $R^{15}$ and $R^{16}$ is a hydroxyl group and the other is a hydrogen atom or a hydroxyl group) according to the method described in process (B) above.

The compounds of formulae (5), (6) and (7) are known compounds described in EP-A-161102 and GB-A-2175587.

The intermediates of formula (2) are novel compounds and form a further aspect of the invention. Key intermediates of formula (2) are those in which $R^3$ is a hydrogen atom, $R^6$ is a hydrogen atom and $R^7$ is a group —OP(O)(X$^1$)(X$^2$) where X$^1$ and X$^2$ both represent OX$^3$. Such intermediates in which X$^3$ is benzoylmethyl or, more particularly, benzyl are of special interest.

Where a salt of a compound of formula (1) is formed, the corresponding acid may be obtained by conventional means by addition of a suitable acid e.g. a mineral acid such as hydrochloric acid.

Where a compound of formula (1) is produced in the acid form, a corresponding salt may be obtained by conventional means, e.g. by addition of a base providing the required cation, for example sodium hydroxide or an alkali metal carboxylate such as a sodium carboxylate (eg sodium 2-ethylhexanoate). Thus, a salt of a compound of formula (1) may be prepared by treating a compound of formula (1) in the acid form with a suitable base in a solvent such as water, an ether eg tetrahydrofuran or an alcohol eg isopropyl alcohol or a mixture thereof. The reaction may conveniently be carried out at ambient temperature. Alternatively, a salt of a compound of formula (1) may be obtained by treating a suitable compound of formula (2) with an alkali metal halide (eg lithium iodide, sodium iodide or potassium iodide) in a suitable solvent such as water or a ketone (eg acetone or butan-2-one) or a mixture thereof, conveniently at ambient temperature. An amino acid salt of a compound of formula (1) may be obtained by treating a compound of formula (1) in the acid form with an amino acid, eg L-arginine monohydrate in water at ambient temperature.

A salt of a compound of formula (1) may be converted to a different salt, eg a physiologically acceptable salt, by exchange of ion using conventional means.

When a specific enantiomer of formula (1) is required, this may be prepared by conventional methods of resolution known per se. Thus, for example, racemic compounds of the invention may be resolved as salts with optically active bases, eg (+)-dehydroabietylamine or (R)-(+)- or (S)-(−)-α-methylbenzylamine. Alternatively, optically active compounds of formula (1) may be prepared from optically active intermediates, eg optically active intermediates of formula (5). Racemic compounds of formula (5) in which $R^{12}$ is hydrogen may be resolved, for example, as salts with optically active bases as above or with optically active acids, eg (L)-(+)- or (D)-(−)-tartaric acid. Compounds of formula (5) in which $R^{12}$ is CHO or COCH$_3$ may be similarly resolved as salts with optically active bases.

The following non-limiting Examples illustrate the invention. All temperatures are in °C. Unless otherwise stated all UV spectral data relate to solutions in ethanol of the compounds concerned.

INTERMEDIATE 1

Juglone 5-bis(phenylmethyl)phosphate

A solution of sulphuryl chloride (3.48 g) in toluene (25 ml) was added to a stirred solution of dibenzyl phosphite (6.08 ml) in toluene (75 ml) under nitrogen. The mixture was stirred for 75 min. under nitrogen, washed with 8% sodium bicarbonate solution (75 ml) and the organic layer separated and dried over anhydrous sodium sulphate. After filtration the filtrate was evaporated and dried to give dibenzyl chlorophosphate (7.75 g) as a colourless oil. Potassium carbonate (1.81 g) was added to a solution of 5-hydroxy-1,4-naphthalenedione (2.18 g) in acetonitrile (300 ml) with stirring at room temperature. Freshly prepared dibenzyl chlorophosphate (7.75 g, see above) in acetonitrile (50 ml) was added and the mixture stirred for 20 h. Potassium carbonate (907 mg) was then added and a further quantity (907 mg) of potassium carbonate added after another 24 h. The mixture was evaporated to dryness and dried in vacuo to give an oil. The oil was subjected to column chromatography (silica, 500 g, 70–230 mesh) eluting with dichloromethane:acetone (96:4). Fractions (250 ml) were collected and fractions 4–12 combined and the solvent evaporated. After drying in vacuo the title compound (3.18 g) was obtained as an orange solid; δ(CDCl$_3$) 5.28 (OCH$_2$), 7.38 (Ph).

INTERMEDIATE 2

Bis(phenylmethyl),[5,8,13,14-tetrahydro-14-methyl-8,13-dioxobenz[5,6]isoindolo[2,1-b]isoquinolin-9-yl]phosphate Acetic anhydride (12 ml) was added to a mixture of N-formyl-1,2,3,4-tetrahydroisoquinoline-4-methyl-3-carboxylic acid (625 mg) and intermediate 1 (3.165 g). The reaction mixture was heated at 100° for 30 min with stirring, then cooled and evaporated to dryness under reduced pressure. The resulting oil was dissolved in dichloromethane (5 ml) and ether was added and the solution cooled in an acetone-drikold bath. The resulting yellow solid was collected by filtration and dried at room temperature to give the title compound (1.16 g); δ(CDCl$_3$) 5.2–5.4 (OCH$_2$), 5.23+5.13 (5H) 4.95 (14H), 1.55 (14 CH$_3$).

INTERMEDIATE 3

5,8,13,14-Tetrahydro-9-hydroxy-14-methylbenz[5,6]isoindolo[2,1-b]isoquinolin-8,13-dione Water (312 ml) and concentrated hydrochloric acid (169 ml) were added to a suspension of 5,8,13,14-tetrahydro-9-[iodoacetoxy]-14-methylbenz[5,6]isoindolo[2,1-b]isoquinolin-8,13-dione (80.0 g, Intermediate 9 in GB-A-2175587) in tetrahydrofuran (1.335 L). This mixture was stirred and heated to reflux under nitrogen for 18 h and part (550 ml) of the solvent was removed by distillation at atmospheric pressure. The resulting suspension was stirred and cooled to ca. 5° for 4.5 h, and the solid was collected by filtration, washed with cold tetrahydrofuran and dried in vacuo to give the title compound (48.8 g); $\lambda_{max}$ 243 nm (MeOH), $E_1^1$ 1022; δ(CDCl$_3$) 12.98 (OH, s, 1H), 5.27 (5-H, d, 16 Hz, 1H), 5.16 (5-H, d, 16 Hz, 1H), 4.98 (14-H, q, 7 Hz, 1H), 1.55 (14-CH$_3$, d, 7 Hz, 3H).

INTERMEDIATE 4

Dimethyl,[5,8,13,14-tetrahydro-14-methyl-8,13-dioxobenz[5,6]isoindolo[2,1-b]isoquinolin-9-yl]phosphate (a) A 60%-dispersion of sodium hydride in oil (200 mg) was washed free of oil with 40°–60° petroleum spirit (2×10 ml) under a nitrogen atmosphere. Dry tetrahydrofuran (25 ml) was added to the sodium hydride, followed by addition of Intermediate 3 (1.5 g) in dry tetrahydrofuran (150 ml). The resulting solution was stirred at 20° under nitrogen for 15 min and then treated with a solution of freshly distilled dimethylchloro phosphate (723 mg) in dry tetrahydrofuran (5 ml). After 1 h the reaction mixture was diluted with water (500 ml) and extracted with dichloromethane (3×250 ml). The combined organic extracts were dried over anhydrous sodium sulphate and evaporated to a green foam which was purified by column chromatography on silica (100 g) eluting with dichloromethane-methanol (29:1) to give the title compound as a green foam (1.539 g); $\lambda_{max}$ 241.6 nm, $E_1^1$ 1052, 369.4 nm, $E_1^1$ 158; δ(CDCl$_3$) 5.26 (5-H, d, 17 Hz, 1H), 5.14 (5-H, d, 17 Hz, 1H), 4.96 (14-H, q, 7 Hz, 1H), 4.02 (OCH$_3$, m, 6H), 1.57 (14-CH$_3$, d, 7 Hz, 3H).

The following compounds were prepared in a similar manner using Intermediate 3 and the appropriate halophosphate:

(b)

Diethyl,[5,8,13,14-tetrahydro-14-methyl-8,13-dioxobenz[5,6]isoindolo[2,1-b]isoquinolin-9-yl]phosphate, (5.609 g) from Intermediate 3 (4.0 g) and diethyl chlorophosphate (2.305 g); $\lambda_{max}$ 243.5 nm, $E_1^1$ 1007, 372 nm, $E_1^1$ 155; δ(CDCl$_3$) 5.23 (5-H, d, 16 Hz, 1H), 5.13 (5-H, d, 16 Hz, 1H), 4.93 (14-H, q, 7 Hz, 1H), 4.37 (OCH$_2$CH$_3$, m, 4H), 1.55 (14-CH$_3$, d, 7 Hz, 3H), 1.38 (OCH$_2$CH$_3$, m, 6H).

(c)

Dipropyl,[5,8,13,14-tetrahydro-14-methyl-8,13-dioxobenz[5,6]isoindolo[2,1-b]isoquinolin-9-yl]phosphate, (2.068 g) from Intermediate 3 (2.0 g) and dipropyl chlorophosphate (1.339 g); $\lambda_{max}$ 242.4 nm, $E_1^1$ 940, 369.6 nm, $E_1^1$ 132; δ(CDCl$_3$) 5.25 (5-H, d, 16 Hz, 1H), 5.15 (5-H, d, 16 Hz, 1H), 4.95 (14-H, q, 7 Hz, 1H), 4.27 (OCH$_2$CH$_2$CH$_3$, m, 4H), 1.76 (OCH$_2$CH$_2$CH$_3$, m, 4H), 1.56 (14-CH$_3$, d, 7 Hz, 3H), 0.97 (OCH$_2$CH$_2$CH$_3$, m, 6H).

(d)
Bis(1-methylethyl),[5,8,13,14-tetrahydro-14-methyl-8,13-dioxobenz[5,6]isoindolo[2,1-b]isoquinolin-9-yl]phosphate, (1.563 g) from Intermediate 3 (1.5 g) and diisopropyl chlorophosphate (1.003 g); λ$_{max}$ 241.8 nm, $E_1^1$ 880, 369.6 nm, $E_1^1$ 132; δ(CDCl$_3$) 5.25 (5-H, d, 16 Hz, 1H), 5.15 (5-H, d, 16 Hz, 1H), 4.85–5.10 (14-H+OCH(CH$_3$)$_2$, m, 3H), 1.56 (14-CH$_3$, d, 7 Hz, 3H), 1.30–1.45 (OCH(CH$_3$)$_2$, m, 12H).

(e)
Dibutyl,[5,8,13,14-tetrahydro-14-methyl-8,13-dioxobenz[5,6]isoindolo[2,1-b]isoquinolin-9-yl]phosphate, (1.628 g) from Intermediate 3 (1.5 g) and dibutyl chlorophosphate (1.143 g); λ$_{max}$ 241.8 nm, $E_1^1$ 956, 369.8 nm, $E_1^1$ 129; δ(CDCl$_3$) 5.25 (5-H, d, 16 Hz, 1H), 5.15 (5-H, d, 16 Hz, 1H), 4.96 (14-H, q, 7 Hz, 1H), 4.31 (OCH$_2$CH$_2$CH$_2$CH$_3$, m, 4H), 1.62–1.80 (OCH$_2$CH$_2$CH$_2$CH$_3$, m, 4H), 1.56 (14-CH$_3$, d, 7 Hz, 3H), 1.32–1.52 (OCH$_2$CH$_2$CH$_2$CH$_3$, m, 4H), 0.92 (OCH$_2$CH$_2$CH$_2$CH$_3$, m, 6H).

(f)
Bis(tetrahydro-2-furanylmethyl),[5,8,13,14-tetrahydro-14-methyl-8,13-dioxobenz[5,6]isoindolo[2,1-b]isoquinolin-9-yl]phosphate, (1.00 g) from Intermediate 3 (2.0 g) and bis(tetrahydro-2-furanylmethyl) chlorophosphate (6.78 g, freshly prepared from phosphorus trichloride and tetrahydrofurfuryl alcohol) except that purification was initially carried out by column chromatography on silica (650 g) eluting with dichloromethane-acetone (4:1) and the resulting yellow foam further purified by column chromatography on silica (70 g) eluting with dichloromethane-methanol (96:4); λ$_{max}$ 242.2 nm, $E_1^1$ 809, 369.8 nm, $E_1^1$ 117; δ(CDCl$_3$), 5.24 (5-H, d, 17 Hz, 1H); 5.16 (5-H, d, 17 Hz, 1H); 4.96 (14-H, q, 7 Hz, 1H); 4.30 (POCH$_2$, m, 4H), 4.21 (OCH$_2$CHO, m, 2H); 1.56 (14-CH$_3$, d, 7 Hz, 3H)

(g) Cyclohexyl methyl,
[5,8,13,14-tetrahydro-14-methyl-8,13-dioxobenz[5,6]isoindolo[2,1-b]isoquinolin-9-yl]phosphate, (1.409 g) from Intermediate 3 (3.0 g) and cyclohexyl methyl chlorophosphate (2.9 g, freshly prepared from methyl dichlorophosphate and cyclohexanol); λ$_{max}$ 242.4 nm, $E_1^1$ 899, 369.6 nm, $E_1^1$ 150; δ(CDCl$_3$) 5.23 (5-H, d, 16 Hz, 1H), 5.13 (5-H, d, 16H, 1H), 4.95 (14-H, q, 7 Hz, 1H), 4.64 (OCH, m, 1H), 4.01 (OCH$_3$, m, 3H), 1.54 (14-CH$_3$, d, 7H$_3$, 3H).

(h)
Bis(2-propenyl),[5,8,13,14-tetrahydro-14-methyl-8,13-dioxobenz[5,6]isoindolo[2,1-b]isoquinolin-9-yl]phosphate, (3.554 g) from Intermediate 3 (3.0 g) and diallyl chlorophosphate (2.68 g) except that purification was carried out by column chromatography on silica (300 g) eluting with dichloromethane-acetone (94:4); λ$_{max}$ 242.2 nm, $E_1^1$ 973, 371.8 nm, $E_1^1$ 148; δ(CDCl$_3$), 5.90–6.10 (CH, m, 2H), 5.20–5.45 (CH$_2$, m, 4H), 5.25 (5-H, d, 17 Hz, 1H), 5.15 (5-H, d, 17 Hz, 1H), 4.94 (14-H, q, 7 Hz, 1H) 4.75–4.90 (OCH$_2$, m, 4H), 1.58 (14-CH$_3$, d, 7H$_3$, 3H).

(i)
Dipentyl,[5,8,13,14-tetrahydro-14-methyl-8,13-dioxobenz[5,6]isoindolo[2,1-b]isoquinolin-9-yl]phosphate, (2.07 g) from Intermediate 3 (2.0 g) and dipentyl chlorophosphate (1.715 g, freshly prepared from phosphorus trichloride and pentan-1-ol) except that after evaporation the oil was dissolved in diethyl ether (50 ml), stirred at 20° for 30 min. and the resulting yellow solid filtered and washed with diethyl ether; λ$_{max}$ 242.4 nm, $E_1^1$ 913, 369.4 nm, $E_1^1$ 137; δ(CDCl$_3$) 5.24 (5-H, d, 17 Hz, 1H), 5.14 (5-H, d, 17 Hz, 1H), 4.96 (14-H, q, 7 Hz, 1H), 4.20–4.40 (POCH$_2$CH$_2$CH$_2$CH$_2$CH$_3$, m, 4H), 1.65–1.85 (POCH$_2$CH$_2$CH$_2$CH$_2$CH$_3$, m, 4H), 1.56 (14-CH$_3$, d, 7 Hz, 3H), 1.20–1.45 (POCH$_2$CH$_2$CH$_2$CH$_2$CH$_3$, m, 8H), 0.88 (POCH$_2$CH$_2$CH$_2$CH$_2$CH$_3$, m, 6H).

(j)
Bis(2-methoxyethyl),[5,8,13,14-tetrahydro-14-methyl-8,13-dioxobenz[5,6]isoindolo[2,1-b]isoquinolin-9-yl]phosphate (2.07 g) from Intermediate 3 (2.0 g) and bis(2-methoxyethyl) chlorophosphate (1.55 g, freshly prepared from 2-methoxyethanol and phosphorus oxychloride) except that the column was eluted with dichloromethane-acetone (4:1); λ$_{max}$ 242.2 nm, $E_1^1$ 920, 371.6 nm, $E_1^1$ 142; δ(CDCl$_3$), 5.23 (5-H, d, 17 Hz, 1H), 5.13 (5-H, d, 17 Hz, 1H), 4.95 (14-H, q, 7 Hz, 1H), 4.48 (POCH$_2$, m, 4H), 3.68 (POCH$_2$CH$_2$, m, 4H), 3.39 (OCH$_3$, s, 3H), 3.40 (OCH$_3$, s, 3H), 1.57 (14-CH$_3$, d, 7 Hz, 3H).

(k)
Bis(cyclohexylmethyl),[5,8,13,14-tetrahydro-14-methyl-8,13-dioxobenz[5,6]isoindolo[2,1-b]isoquinolin-9-yl]phosphate (5.302 g) from Intermediate 3 (4.0 g) and bis(cyclohexylmethyl) chlorophosphate (8.22 g, freshly prepared from phosphorus trichloride and cyclohexylmethanol) except that after evaporation the solid was triturated with ether (100 ml) and crystallised from ethyl acetate/chloroform; λ$_{max}$ 242.4 nm, $E_1^1$ 778, 369.6 nm, $E_1^1$ 119; δ(CDCl$_3$) 5.25 (5-H, d, 16 Hz, 1H), 5.15 (5-H, d, 16 Hz, 1H), 4.96 (14-H, q, 7 Hz, 1H), 4.09 (OCH$_2$, m, 4H), 1.54 (14-CH$_3$, d, 7 Hz, 3H).

INTERMEDIATE 5

(a)
Bis(phenylmethyl),[5,8,13,14-tetrahydro-14-methyl-8,13-dioxobenz[5,6]isoindolo[2,1-b]isoquinolin-9-yl]phosphate N-chlorosuccinimide (1.017 g) was added to a stirred solution of dibenzyl phosphite (3.3 ml) in dry benzene (30 ml) and the resulting solution was stirred at 20°, the succinimide was removed by filtration and the filtrate was concentrated to a low volume (about 5–10 ml). This solution was then used in the following preparation.

A 60%-dispersion of sodium hydride in oil (134 mg) was washed free of oil with 40°–60° petroleum spirit (2×15 ml) under a nitrogen atmosphere. Dry tetrahydrofuran (25 ml) was added to the sodium hydride followed by addition of Intermediate 3 (1.0 g) in dry tetrahydrofuran (100 ml). The resulting red solution was cooled to 10° in an ice-bath and treated with freshly prepared dibenzyl chlorophosphate in benzene (about 5–10 ml, see above). After 2 h at 10°, the reaction mixture was allowed to warm to 20° and maintained at this temperature for 3 h. The reaction mixture was diluted with water (500 ml) and extracted with dichloromethane (3×250 ml). The combined organic extracts were dried over anhydrous sodium sulphate and evaporated to a green oil which was dissolved in dichloromethane and applied to a column of silica (300 g) prepared using dichloromethane-acetone (96:4). The column was eluted with dichloromethane-acetone (96:4) and 25 ml fractions were collected. The product-containing fractions were combined and evaporated to yield the title compound as a green foam (1.211 g); $\lambda_{max}$ 244 nm, $E_1^1$ 743, 374 nm, $E_1^1$ 112; $\delta$(CDCl$_3$) 5.20–5.40 (OCH$_2$C$_6$H$_5$, m, 4H), 5.23 (5-H, d, 16 Hz, 1H), 5.13 (5-H, d, 16 Hz, 1H), 4.95 (14-H, q, 7 Hz, 1H), 1.55 (14-CH$_3$, d, 7 Hz, 3H).

The following compound was prepared in a similar manner:

(b)

Bis[(4-nitrophenyl)methyl],[5,8,13,14-tetrahydro-14-methyl-8,13-dioxobenz[5,6]isoindolo[2,1-b]isoquinolin-9-yl]phosphate, (3.662 g) from Intermediate 3 (2.0 g) and di(p-nitrobenzyl) chlorophosphate (2.582 g); $\lambda_{max}$ 244 nm, $E_1^1$ 330; $\delta$(d$_6$-DMSO) 5.48 (OCH$_2$, d, 8 Hz, 4H), 5.42 (5-H, d, 18 Hz, 1H), 5.32 (5-H, d, 18 Hz, 1H), 4.79 (14-H, q, 7 Hz, 1H), 1.48 (14-CH$_3$, d, 7 Hz, 3H).

INTERMEDIATE 6

5,8,13,14-Tetrahydro-12-hydroxy-14-methylbenz[5,6]isoindolo[2,1-b]isoquinolin-8,13-dione Acetic anhydride (160 ml) was added to a mixture of N-formyl-1,2,3,4-tetrahydroisoquinoline-4-methyl-3-carboxylic acid (20 g) and 5-hydroxy-1,4-naphthoquinone (31.78 g). The reaction mixture was heated at 100° for 30 min and then left to cool (4°) overnight. A precipitate formed which was filtered, washed with ether, dried in vacuo and purified by column chromatography on silica gel eluting with dichloromethane to yield the title compound; $\lambda_{max}$ 243 nm, $E_1^1$ 1103, 397 nm, $E_1^1$ 381.

INTERMEDIATE 7

Bis(phenylmethyl),[7-bromo-5,8,13,14-tetrahydro-14-methyl-8,13-dioxobenz[5,6]isoindolo[2,1-b]isoquinolin-9-yl]phosphate To a solution of Intermediate 5(a) (1.0 g) in dichloromethane (50 ml) was added N-bromosuccinimide (0.604 g) in dichloromethane (50 ml). After 1 h at 20°, the reaction mixture was evaporated and the residue was purified by column chromatography, firstly on silica (150 g) eluting with chloroform-acetone (96/4) followed by silica (40 g) eluting with dichloromethane-acetone (96/4) to give the title compound as a brown foam (0.81 g); $\lambda_{max}$ 242.0 nm, $E_1^1$ 760, 378.0 nm, $E_1^1$ 108; $\delta$(d$_6$-DMSO) 5.42 (5-H, d, 17 Hz, 1H), 5.34–5.17 (5-H+OCH$_2$, m, 5H), 4.89 (14-H, q, 7 Hz, 1H), 1.49 (14-CH$_3$, d, 7 Hz, 3H).

INTERMEDIATE 8

Bis(phenylmethyl),[7-chloro-5,8,13,14-tetrahydro-14-methyl-8,13-dioxobenz[5,6]isoindolo[2,1-b]isoquinolin-9-yl]phosphate To a solution of Intermediate 5(a) (1.0 g) in chloroform (200 ml) was added N-chlorosuccinimide (0.226 g) followed by a saturated solution of hydrogen chloride in chloroform (0.5 ml). After 30 min at 20°, the reaction mixture was evaporated to a yellow foam which was purified by column chromatography on silica (100 g) eluting with dichloromethane-acetone (96/4) to give a yellow foam (0.943 g). Crystallisation of this foam from acetone gave the title compound as a yellow solid (0.697 g); $\lambda_{max}$ 241.6 nm, $E_1^1$ 820, 377.2 nm, $E_1^1$ 125; $\delta$(d$_6$-DMSO) 5.43 (5-H, d, 17 Hz, 1H), 5.32–5.16 (5-H+OCH$_2$, m, 5H), 4.87 (14-H, q, 7 Hz, 1H), 1.49 (14-CH$_3$, d, 7 Hz, 3H).

INTERMEDIATE 9

Bis(2-oxo-2-phenylethyl),[5,8,13,14-tetrahydro-14-methyl-8,13-dioxobenz[5,6]isoindolo[2,1-b]isoquinolin-9-yl]phosphate A solution of dicyclohexylcarbodiimide (3.03 g) in dichloromethane (125 ml) was added dropwise over 3 h to a stirred solution of phosphoric acid bis(2-oxo-2-phenylethyl) ester (8.93 g) in dichloromethane (500 ml) at 20° C. The reaction mixture was evaporated to low volume (ca. 100 ml) and the precipitated solid was removed by filtration. The filtrate was stirred at 20° for 1 h and then evaporated to give the crude phosphorylating reagent as a colourless oil.

A 60% dispersion of sodium hydride in oil (534 mg) was washed free of oil with 40°–60° petroleum ether (2×25 ml) under a nitrogen atmosphere. Dry tetrahydrofuran (100 ml) was added to the sodium hydride followed by a solution of Intermediate 3 (4 g) in dry tetrahydrofuran (400 ml). The resulting solution was stirred at 20° for 30 min. and then treated with the crude phosphorylating reagent. After 15 min. at 20° the reaction mixture was diluted with water (2.5 L) and extracted with dichloromethane (3×600 ml). The organic extracts were dried over anhydrous sodium sulphate and evaporated to a yellow solid (8.96 g). To this solid (7.96 g) was added acetone (200 ml) and insoluble impurities were removed by filtration. The filtrate was evaporated and the residue was subjected to column chromatography on silica (270 g) eluting with dichloromethane-methanol (96/4) to give a yellow foam. This foam was purified by further column chromatography on silica (100 g) eluting with dichloromethane-acetone (96/4) to give the title compound as a yellow foam (1.14 g); I.R. (CHBr$_3$) 1710 cm$^{-1}$, 1659 cm$^{-1}$; $\delta$(CDCl$_3$) 5.68–7.81 (OCH$_2$, m, H), 5.22 (5-H, d, 16 Hz, 1H), 5.15 (5-H, d, 16 Hz, 1H), 4.95 (14-H, q, 7 Hz, 1H), 1.55 (14-CH$_3$, d, 7 Hz, 3H).

INTERMEDIATE 10

(a)

Diethyl,[5,8,13,14-tetrahydro-14-methyl-8,13-dioxobenz[5,6]isoindolo[2,1-b]isoquinolin-12-yl]phosphate A 50% dispersion of sodium hydride in oil (158 mg) was washed free of oil with 40°–60° petroleum spirit (2×10 ml) under a nitrogen atmosphere. Dry tetrahydrofuran (25 ml) was added to the sodium hydride followed by addition of Intermediate 6 (1.0 g) in dry tetrahydrofuran (100 ml). The resulting solution was stirred at 20° under nitrogen for 15 min and then treated with a solution of freshly distilled diethyl chlorophosphate (569 mg) in dry tetrahydrofuran (5 ml). After 1.5 h, the reaction mixture was diluted with water (500 ml) and extracted with dichloromethane (3×250 ml). The combined organic extracts were dried over anhydrous sodium sulphate and evaporated to a green solid (1.484 g)

which was purified by column chromatography on silica (150 g) eluting with chloroform-ethanol (49/1) to give a green solid (1.254 g). Crystallisation of this solid from a mixture of chloroform and ethyl acetate gave the title compound as green feathery crystals (904 mg); $\lambda_{max}$ 243 nm, $E_1^1$ 1005, 372 nm, $E_1^1$ 146; δ(CDCl$_3$) 5.25 (5-H, d, 16 Hz, 1H), 5.15 (5-H, d, 16 Hz, 1H), 5.01 (14-H, q, 7 Hz, 1H) 4.39 (OCH$_2$CH$_3$, m, 4H), 1.54 (14-CH$_3$, d, 7 Hz, 3H), 1.42 (OCH$_2$CH$_3$, m, 6H).

The following compound was prepared in a similar manner:

(b)

Bis(phenylmethyl),[5,8,13,14-tetrahydro-14-methyl-8,13-dioxobenz[5,6]isoindolo[2,1-b]isoquinolin-12-yl]phosphate (1.5 g) from Intermediate 6 (3.0 g) and dibenzyl chlorophosphate (freshly prepared from dibenzyl phosphate (9.9 ml) and N-chlorosuccinimide) in benzene (ca. 20 ml) except that elution was carried out using dichloromethane-acetone (96:4) to give an oil which crystallised on standing and was recrystallised from ethyl acetate/chloroform; $\lambda_{max}$ 242.6 nm, $E_1^1$ 733, 371.4 nm, $E_1^1$ 109; δ(CDCl$_3$) 5.20-5.45 (OCH$_2$+5-H, m, 5H), 5.15 (5-H, d, 16 Hz, 1H), 4.97 (14-H, q, 7 Hz, 1H), 1.53 (14-CH$_3$, d, 7 Hz, 3H).

INTERMEDIATE 11

Dipropyl,[1,4-dioxonaphthalene-5,8-diyl]phosphate 5,8-Dihydroxy-1,4-naphthalenedione (1 g ) was suspended in acetone (100 ml) and potassium carbonate (4 g) and dipropyl chlorophosphate (5 ml) were added. The reaction mixture was stirred at 40°–50° for 90 min., filtered to remove excess potassium carbonate and evaporated to dryness. The residue was dissolved in dichloromethane and purified by column chromatography on silica using dichloromethane and dichloromethane-methanol (99:1) as eluant to give the title compound as a yellow oil (2.31 g); δ(CDCl$_3$) 4.23 (CH$_2$), 1.78 (CH$_2$), 1.01 (CH$_3$).

INTERMEDIATE 12

Dipropyl,[5,8,13,14-tetrahydro-14-methyl-8,13-dioxobenz[5,6]isoindolo[2,1-b]isoquinolin-9,12-diyl]phosphate Acetic anhydride (10 ml) was added to a mixture of N-formyl-1,2,3,4-tetrahydroisoquinoline-4-methyl-3-carboxylic acid (440 mg) and Intermediate 11 (2.16 g). The reaction mixture was kept at 10° for 30 min. and then evaporated to dryness to give a brown oil. Chromatography on silica using petrol (60°–80°)-ethyl acetate (1:1, 1:2 and 1:3) as eluant gave the title compound (984 mg); $\lambda_{max}$ 237.6 nm, $E_1^1$ 609, 371 nm, $E_1^1$ 94; δ(CDCl$_3$) 5.13+5.23 (5H), 4.93 (14H), 4.20-4.35 (CH$_2$), 1.60-1.90 (CH$_2$), 0.8-1.05 (CH$_3$).

EXAMPLE 1

[5,8,13,14-Tetrahydro-14-methyl-8,13-dioxobenz[5,6]isoindolo[2,1-b]isoquinolin-9-yl]dihydrogen phosphate, disodium salt A cooled solution (0° to 5°) of Intermediate 4(b) (465 mg) in carbon tetrachloride (3 ml) was treated under a nitrogen atmosphere with trimethylsilyl iodide (0.32 ml). After 5 min, the reaction mixture was evaporated to dryness and the residual oil was treated with methanol (5 ml). The mixture was stirred at 20° and after about 5 min a clear brown solution was obtained. After 20 min the solution was evaporated to a dark foam which was suspended in water (20 ml) and the suspension adjusted to pH 7.5 with 1M-sodium hydroxide solution (4.00 ml). The resulting mixture was extracted with chloroform (25 ml) and was filtered through a prewashed bed of kieselguhr using water (50 ml) to wash the product through. The resulting layers were separated and the aqueous phase was washed with more chloroform (10 ml). The combined aqueous extracts were filtered through a millipore filter, degassed and freeze-dried. The freeze-dried solid was redissolved in water (100 ml) filtered through a millipore filter and freeze-dried to give the title compound as a bright yellow solid (0.398 g); $\lambda_{max}$ 246 nm, $E_1^1$ 667, 388 nm, $E_1^1$ 165.

EXAMPLE 2

(a)

Phenylmethyl,[5,8,13,14-tetrahydro-14-methyl-8,13-dioxobenz[5,6]isoindolo[2,1-b]isoquinolin-9-yl]phosphoric acid, sodium salt Sodium iodide (1.551 g) was added to a solution of Intermediate 5(a) (5.546 g) in acetone (100 ml) and the resulting solution was heated under reflux for 1.5 h. The reaction mixture was evaporated to dryness and the residue was triturated with ether (100 ml) to give a yellow solid. This solid was dissolved in water (200 ml) and the pH of the solution was adjusted to pH 1 to 2 by the addition of 2M-hydrochloric acid. The resulting mixture was diluted with water (200 ml) and extracted with dichloromethane (2×400 ml). Salt solution was added during the extraction procedure to disperse the emulsion which was formed. The combined organic extracts were dried over anhydrous sodium sulphate and evaporated to a green solid. This solid was suspended in water (300 ml) and the suspension was adjusted to pH 7.0 by the dropwise addition of 1M-sodium hydroxide solution. The resulting solution was filtered and the filtrate was freeze-dried to a solid which was treated with acetone (400 ml) and evaporated to dryness to give a solid (4.49 g). Trituration of this solid with ether (200 ml) gave the title compound as a yellow solid (4.232 g); $\lambda_{max}$ 243.8 nm, $E_1^1$ 679, 367.2 nm, $E_1^1$ 132; δ(d$_6$-DMSO) 5.41 (5-H, d, 16 Hz, 1H), 5.31 (5-H, d, 16 Hz, 1H), 4.93 (OCH$_2$, d, 6 Hz, 2H), 4.82 (14-H, q, 7 Hz, 1H), 1.47 (14-CH$_3$, d, 7 Hz, 3H).

The following compounds were prepared in a similar manner:

(b)

Propyl,[5,8,13,14-tetrahydro-14-methyl-8,13-dioxobenz[5,6]isoindolo[2,1-b]isoquinolin-9-yl]phosphoric acid, sodium salt, (1.256 g) from Intermediate 4(c) (1.5 g) and sodium iodide (1.367 g) using butan-2-one (35 ml) in place of acetone; $\lambda_{max}$ 243.6 nm, $E_1^1$ 963, 360.0 nm, $E_1^1$ 265; δ(d$_6$-DMSO) 5.42 (5-H, d, 16 Hz, 1H), 5.32 (5-H, d, 16 Hz, 1H), 4.81 (14-H, m, 1H), 3.78 (OCH$_2$CH$_2$CH$_3$, m, 2H), 1.40-1.60 (14-CH$_3$+OCH$_2$CH$_2$CH$_3$, m, 3H), 0.82 (OCH$_2$CH$_2$CH$_3$, m, 3H).

(c)

(1-Methylethyl),[5,8,13,14-tetrahydro-14-methyl-8,13-dioxobenz[5,6]isoindolo[2,1-b]isoquinolin-9-yl]phosphoric acid, sodium salt, (910 mg) from Intermediate 4(d) (1.2 g) and sodium iodide (1.094 g) using butan-2-one (25 ml) in place of acetone; $\lambda_{max}$ 243.4 nm, $E_1^1$ 943, 366.8 nm, $E_1^1$ 199; δ(d$_6$-DMSO) 5.40 (5-H, d, 16 Hz, 1H), 5.30 (5-H, d, 16 Hz, 1H), 4.81 (14-H, q, 7 Hz, 1H), 4.43 (OCH(CH$_3$)$_2$, m, 1H), 1.48 (14-CH$_3$, d, 7 Hz, 3H), 1.11 (OCH(CH$_3$)$_2$, d, 5 Hz, 6H).

(d)

Phenylmethyl,[7-bromo-5,8,13,14-tetrahydro-14-methyl-8,13-dioxobenz[5,6]isoindolo[2,1-b]isoquinolin-9-yl]phosphoric acid, sodium salt, (338 mg) from Intermediate 7 (705 mg) and sodium iodide (174 mg); $\lambda_{max}$ 243.6 nm, $E_1^1$ 601, 367.8 nm, $E_1^1$ 120; δ(d$_6$-DMSO) 5.40 (5-H, d, 17 Hz, 1H), 5.21 (5-H, d, 17 Hz, 1H), 4.97–4.82 (14-H+OCH$_2$, m, 3H), 1.48 (14-CH$_3$, d, 7 Hz, 3H).

(e)

Phenylmethyl,[7-chloro-5,8,13,14-tetrahydro-14-methyl-8,13-dioxobenz[5,6]isoindolo[2,1-b]isoquinolin-9-yl]phosphoric acid, sodium salt, (674 mg) from Intermediate 8 (1.068 g) and sodium iodide (282 mg); $\lambda_{max}$ 243.0 nm, $E_1^1$ 688, 374.0 nm, $E_1^1$ 98; δ(d$_6$-DMSO) 5.40 (5-H, d, 17 Hz, 1H), 5.23 (5-H, d, 17 Hz, 1H), 5.00–4.79 (14-H+OCH$_2$, m, 3H), 1.50 (14-CH$_3$, d, 7 Hz, 3H).

(f)

Pentyl,[5,8,13,14-tetrahydro-14-methyl-8,13-dioxobenz[5,6]isoindolo[2,1-b]isoquinolin-9-yl]phosphoric acid, sodium salt (0.836 g) from Intermediate 4(i) (1.207 g) and sodium iodide (724 mg) using butan-2-one (30 ml) in place of acetone; $\lambda_{max}$ 244.0 nm, $E_1^1$ 899, 366.8 nm, $E_1^1$ 190; δ(d$_6$-DMSO) 5.40 (5-H, d, 17 Hz, 1H), 5.32 (5-H, d, 17 Hz, 1H), 4.81 (14-H, q, 7 Hz, 1H), 3.80 (POCH$_2$CH$_2$CH$_2$CH$_2$CH$_3$, 4$^{et}$, 7 Hz, 2H), 1.35–1.55 (POCH$_2$CH$_2$CH$_2$CH$_2$CH$_3$+14-CH$_3$, m, 5H), 1.10–1.30 (POCH$_2$CH$_2$CH$_2$CH$_2$CH$_3$, m, 4H), 0.79 (POCH$_2$CH$_2$CH$_2$CH$_2$CH$_3$, t, 7 Hz, 3H).

(g)

Cyclohexylmethyl,[5,8,13,14-tetrahydro-14-methyl-8,13-dioxobenz[5,6]isoindolo[2,1-b]isoquinolin-9-yl]phosphoric acid, sodium salt (1.017 g) from Intermediate 4(k) (1.5 g) and sodium iodide (411 mg) using butan-2-one (40 ml) in place of acetone; $\lambda_{max}$ 244.0 nm, $E_1^1$ 849, 366.8 nm, $E_1^1$ 198; δ(d$_6$-DMSO) 5.41 (5-H, d, 16 Hz, 1H), 5.31 (5-H, d, 16 Hz, 1H), 4.81 (14-H, q, 7 Hz, 1H), 3.62 (OCH$_2$, t, 6 Hz, 2H), 1.48 (14-CH$_3$, d, 7 Hz, 3H).

(h)

Phenylmethyl,[5,8,13,14-tetrahydro-14-methyl-8,13-dioxobenz[5,6]isoindolo[2,1-b]isoquinolin-12-yl]phosphoric acid, sodium salt (781 mg) from Intermediate 10(b) (1.2 g) and sodium iodide (336 mg) except that after the pH was adjusted with hydrochloric acid the resulting mixture was extracted with dichloromethane-methanol (3:2, 400 ml and 2×200 ml); $\lambda_{max}$ 244.0 nm, $E_1^1$ 842, 265.8 nm, $E_1^1$ 295, 356.0 nm, $E_1^1$ 97; δ(d$_6$-DMSO) 5.41 (5-H, d, 16 Hz, 1H), 5.31 (5-H, d, 16 Hz, 1H), 4.93 (OCH$_2$, d, 7 Hz, 2H), 4.88 (14-H, q, 7 Hz, 1H), 1.47 (14-CH$_3$, d, 7 Hz, 3H).

EXAMPLE 3

(a)

Methyl,[5,8,13,14-tetrahydro-14-methyl-8,13-dioxobenz[5,6]isoindolo[2,1-b]isoquinolin-9-yl]phosphoric acid, sodium salt A mixture of Intermediate 4(a) (1.0 g) and sodium iodide (377 mg) in acetone (35 ml) was heated under reflux for 5 h. After this time, a second portion of sodium iodide (189 mg) was added, and the reaction mixture was maintained under reflux for 1 h. The reaction mixture was cooled to 20° and the precipitated product was collected by filtration, washed with acetone and ether, and dried to give a green solid which was dissolved in water (50 ml) the pH of the resulting solution being adjusted to pH 1 to 2 by the addition of 2M-hydrochloric acid. The resulting mixture was diluted with water (50 ml) and extracted with dichloromethane (2×100 ml). Salt solution was added during the extraction procedure to disperse the emulsion which was formed. The combined organic extracts were dried over anhydrous sodium sulphate and evaporated to a green solid which was suspended in water (70 ml) the resulting suspension being adjusted to pH 7.0 by the dropwise addition of 1M-sodium hydroxide solution. The resulting solution was filtered and the filtrate was freeze-dried to a solid which was suspended in acetone (100 ml) and evaporated to dryness to give a solid. Trituration of this solid with ether (100 ml) gave the title compound as a yellow solid (858 mg); $\lambda_{max}$ 243.4 nm, $E_1^1$ 991, 365.4 nm, $E_1^1$ 199; δ(d$_6$-DMSO) 5.41 (5-H, d, 16 Hz, 1H), 5.31 (5-H, d, 16 Hz, 1H), 4.82 (14-H, q, 7 Hz, 1H) 3.50 (OCH$_3$, d, 11 Hz, 3H) 1.47 (14-CH$_3$, d, 7 Hz, 3H).

The following compounds were prepared in a similar manner:

(b)

Butyl,[5,8,13,14-tetrahydro-14-methyl-8,13-dioxobenz[5,6]isoindolo[2,1-b]isoquinolin-9-yl]phosphoric acid, sodium salt (1.041 g) from Intermediate 4(e) (1.255 g) and sodium iodide (1.082 g); $\lambda_{max}$ 243.2 nm, $E_1^1$ 984, 366.6 nm, $E_1^1$ 189; δ (d$_6$-DMSO) 5.41 (5-H, d, 16 Hz, 1H), 5.31 (5-H, d, 16 Hz, 1H), 4.82 (14-H, q, 7 Hz, 1H), 3.81 (OCH$_2$CH$_2$CH$_2$CH$_3$, q, 6 Hz, 2H), 1.15–1.60 (OCH$_2$CH$_2$CH$_2$CH$_3$+14-CH$_3$, m, 7H), 0.83 (OCH$_2$CH$_2$CH$_2$CH$_3$, t, 6 Hz, 3H).

(c)

Cyclohexyl,[5,8,13,14-tetrahydro-14-methyl-8,13-dioxobenz[5,6]isoindolo[2,1-b]isoquinolin-9-yl]phosphoric acid, sodium salt (6.86 mg) from Intermediate 4(g) (1.0 g) except that the final trituration step was not necessary; $\lambda_{max}$ 244.0 nm, $E_1^1$ 850, 367.0 nm, $E_1^1$ 182; δ (d$_6$-DMSO) 5.42 (5-H, d, 16 Hz, 1H), 5.32 (5-H, d, 16 Hz, 1H), 5.48 (14-H, q, 7 Hz, 1H), 4.13 (OCH, m, 1H), 1.46 (14-CH$_3$, d, 7 Hz, 1H).

EXAMPLE 4

Ethyl,[5,8,13,14-tetrahydro-14-methyl-8,13-dioxobenz[5,6]isoindolo[2,1-b]isoquinolin-9-yl]phosphoric acid, sodium salt Sodium iodide (3.0 g) was added to a solution of Intermediate 4(b) (3.0 g) in acetone (150 ml) and the mixture was heated under reflux for 4 h. After this time, a second portion of sodium iodide (3.0 g) was added, and the reaction mixture was maintained under reflux for 16 h. The reaction mixture was cooled to 20°0 and the precipitated product was collected by filtration, washed with acetone (3×30 ml) and dried to give the title compound as a green solid (2.37 g); $\lambda_{max}$ 244.5 nm, $E_1^1$ 1050, 368.5 nm, $E_1^1$ 222; δ (d$_6$-DMSO) 5.41 (5-H, 16 Hz, 1H), 5.30 (5-H, d, 16 Hz, 1H), 4.82 (14-H, q, 7 Hz, 1H), 3.90 (OC$\underline{H}_2$CH$_3$, m, 2H), 1.49 (14-CH$_3$, d, 7 Hz, 3H), 1.14 (OC$\overline{H}_2\underline{CH}_3$, t, 8 Hz, 3H).

EXAMPLE 5

Phenyl,[5,8,13,14-tetrahydro-14-methyl-8,13-dioxobenz[5,6]isoindolo[2,1-b]isoquinolin-9-yl]phosphoric acid, sodium salt A 60%-dispersion of sodium hydride in oil (67 mg) was washed free of oil with 40–60° petroleum spirit (2×10 ml) under a nitrogen atmosphere. Dry tetrahydrofuran (10 ml) was added to the sodium hydride, followed by addition of Intermediate 3 (500 mg) in dry tetrahydrofuran (50 ml). The resulting solution was stirred at 20° under nitrogen for 15 min and then treated with phenyl dichlorophosphate (381 mg). After 1 h, the reaction mixture was diluted with water (250 ml) and extracted with dichloromethane (3×100 ml). Salt solution was added, during the extraction procedure, to disperse the emulsion which was formed. The combined organic extracts were dried over anhydrous sodium sulphate and evaporated to an oily foam (769 mg). This foam was dissolved in a mixture of tetrahydrofuran (15 ml) and water (5 ml) and basified with 1M-sodium hydroxide solution. After 2 h at pH 9 and 2 $\overline{\text{h}}$ at pH 12, the reaction mixture was warmed to 50–55° and diluted with water (5 ml) and tetrahydrofuran (5 ml). After 20 min, the reaction mixture was concentrated in vacuo, diluted with water (150 ml) and acidified to pH 1 to 2 with 2M-hydrochloric acid. The resulting mixture was extracted with dichloromethane (3×100 ml). Salt solution was added during the extraction procedure to disperse the emulsion which was formed. The combined organic extracts were dried over anhydrous sodium sulphate and evaporated to a dark green foam (705 mg). This foam was suspended in water (100 ml) and the suspension was adjusted to pH 7.1 by the dropwise addition of 1M-sodium hydroxide solution. The reuslting mixture was filtered and the filtrate was freeze-dried to a foam which was treated with acetone (100 ml) and evaporated to dryness to give a solid (440 mg). Trituration of this solid with ether (100 ml) gave the title compound as a dark green solid (341 mg); $\lambda_{max}$ 243.8 nm, $E_1^1$ 918, 369.2 nm, $E_1^1$ 174; δ (d$_6$-DMSO) 5.42 (5-H, d, 16 Hz, 1H), 5.32 (5-H, d, 16 Hz, 1H), 4.82 (14-H, q, 7 Hz, 1H), 1.48 (14-CH$_3$, d, 7 Hz, 3H).

EXAMPLE 6

(4-Nitrophenyl)methyl,[5,8,13,14-tetrahydro-14-methyl-8,13-dioxobenz[5,6]isoindolo[2,1-b]isoquinolin-9-yl]phosphoric acid, sodium salt Sodium iodide (330 mg) was added to a suspension of Intermediate 5(b) (1.359 g) in butan-2-one (100 ml) and the mixture was heated under reflux for 1.5 h. The reaction mixture was evaporated to dryness and the residue was triturated with ether (3×100 ml) to give a green soid (1.055 g). The solid was recovered by filtration to give the title compound as a green solid (911 mg); $\lambda_{max}$ 243.8 nm, $E_1^1$ 837, 265.2 nm, $E_1^1$ 438, 368.8 nm, $E_1^1$ 142; δ (d$_6$-DMSO) 5.39 (5-H, d, 16 Hz, 1H), 5.29 (5-H, d, 16 Hz, 1H), 5.09 (OCH$_2$, d, 7 Hz, 2H) 4.80 (14-H, q, 7 Hz, 1), 1.46 (14-CH$_3$, d, 7 Hz, 3H).

EXAMPLE 7

[5,8,13,14-Tetrahydro-8,13-dioxo-14-methylbenz[5,6]isoindolo[2,1-b]isoquinolin-9-yl]dihydrogen phosphate, disodium salt Intermediate 5(a) (1.6 g) was dissolved in dry carbon tetrachloride (5 ml) and the resulting solution was cooled in an ice-bath at 0° to 5°. The mixture was allowed to warm to 20° and dry carbon tetrachloride (8 ml) was added, followed by dichloromethane (5 ml). The resulting solution was cooled at 0° to 5° under nitrogen and treated with trimethylsilyl iodide (0.54 ml). After 5 min at 0° to 5°, the reaction mixture was evaporated to dryness and the residual oil was treated with methanol (10 ml). The mixture was stirred at 20° and after about 5 min, a clear brown solution was obtained. After 10 min, the solution was evaporated to an oil which was then triturated with diethyl ether (4×25 ml) to give a dark yellow solid which was suspended in sterile water (70 ml). The pH was adjusted to pH 8.0 by the addition of 0.1M-sodium hydroxide solution to give a solution which was filtered through a glass-fibre filter to remove a small amount of coarse solid and then twice through a large (5 cm) millipore filter. The filtrate was freeze-dried to yield the title compound as a dark yellow solid (0.738 g); $\lambda_{max}$ 246 nm, $E_1^1$ 667, 388 nm, $E_1^1$ 165.

EXAMPLE 8

2-Oxo-2-phenylethyl,[5,8,13,14-tetrahydro-14-methyl-8,13-dioxobenz[5,6]isoindolo[2,1-b]isoquinolin-9-yl]phosphoric acid, sodium salt Sodium iodide (243 mg) was added to a solution of Intermediate 9 (1.12 g) in acetone (25 ml). The resulting solution was refluxed for 10 min. and then evaporated. The residue was triturated with ether (3×30 ml) to give a solid. Water (140 ml) was added to this solid and insoluble impurities removed by filtration. the resulting solution was acidified to pH 1.5 by the addition of 2M hydrochloric acid and extracted with dichloromethane (3×300 ml). The organic extracts were dried over anhydrous sodium sulphate and evaporated to a solid. The solid was suspended in water (40 ml) and 0.1M sodium hydroxide solution was added to pH 7.0. The resulting solution was filtered and freeze-dried to a foam. Treatment of this foam with acetone (100 ml) gave a solution which was filtered and evaporated. The residue was triturated with ether (50 ml) to give the title compound as a yellow solid (500 mg); $\lambda_{max}$ 243.6 nm, $E_1^1$ 955, 366.4 nm, $E_1^1$ 147; δ (d$_6$-DMSO) 5.39 (5-H, d, 17 Hz, 1H), 5.30 (5-H, d, 17 Hz, 1H), 5.23 (OCH$_2$, d, 8 Hz, 2H), 4.82 (14-H, q, 7 Hz, 1H), 1.48 (14-CH$_3$, d, 7 Hz, 3H).

EXAMPLE 9

Tetrahydro-2-furanylmethyl,[5,8,13,14-tetrahydro-14-methyl-8,13-dioxobenz[5,6]isoindolo[2,1-b]isoquinolin-9-yl]phosphoric acid, sodium salt Sodium iodide (272 mg) was added to a solution of Intermediate 4(f) (952 mg) in butan-2-one (50 ml). The resulting solution was refluxed for 75 min, further sodium iodide (272 mg) was added and refluxing continued for 24 h. the reaction mixture was evaporated to low volume (ca. 25 ml) and refluxing continued for 24 h. The precipitated solid was filtered and washed with ether (2×40 ml). This solid was dissolved in water (75 ml) and the solution acidified to pH 1.5 by the addition of 2M hydrochloric acid and extracted with dichloromethane (5×750 ml). The organic extracts were dried over anhydrous sodium sulphate and evaporated to a foam. This foam was suspended in water (50 ml) and 0.1M sodium hydroxide solution was added to ph 7.0. The resulting solution was filtered and freeze-dried to a foam. This foam was treated with acetone (50 ml) and the resulting suspension was evaporated. The residue was triturated with ether (50 ml) to give the title compound as a yellow solid (588 mg); $\lambda_{max}$ 244.0 nm, $E_1^1$ 867, 366.2 nm, $E_1^1$ 178; δ (d$_6$-DMSO) 5.40 (5-H, d, 17 Hz, 1H), 5.30 (5-H, d, 17 Hz, 1H), 4.80 (14-H, q, 7 Hz, 1H), 3.50–4.00 (POCH$_2$+OCH$_2$CHO+CH$_2$CH$_2$O (obscured), m, 5H), 1.48 (14-CH$_3$, d, 7 Hz, 3H).

EXAMPLE 10

(2-Propenyl,[5,8,13,14-tetrahydro-14-methyl-8,13-dioxobenz[5,6]isoindolo[2,1-b]isoquinolin-9-yl]phosphoric acid, sodium salt Sodium iodide (697 mg) was added to a solution of Intermediate 4(h) (1.5 g) in acetone (30 ml) and the mixture was heated under reflux. After 3 h, the reaction mixture was cooled to 20° and the precipitated product was collected by filtration, washed with acetone (10 ml) and ether (10 ml) and dried to a yellow solid. This solid was dissolved in water (300 ml) and the pH of the solution was adjusted to pH 1.5 by the addition of 2M-hydrochloric acid. The resulting mixture was extracted with dichloromethane-ethanol (4:1, 300 ml) and then dichloromethane (300 ml). Salt solution was added during the extraction procedure to disperse the emulsion which was formed. The combined organic extracts were dried over anhydrous sodium sulphate and evaporated to a green foam. This foam was suspended in water (150 ml) and the suspension was adjusted to pH 7.0 by addition of 1M-sodium hydroxide solution. The resulting solution was filtered and the filtrate was freeze-dried to a yellow foam. Trituration of this foam with ether (100 ml) gave the title compound as a yellow solid (1.214 g); $\lambda_{max}$ 244.0 nm, $E_1^1$ 883, 367.4 nm, $E_1^1$ 183; δ (d$_6$-DMSO), 5.85–6.00 (CH, m, 1H), 4.95–5.30 (CH$_2$, m, 2H), 5.39 (5-H, d, 17 Hz, 1H), 5.30 (5-H, d, 17 Hz, 1H), 4.82 (14-H, q, 7 Hz, 1H), 4.30–4.50 (OCH$_2$, m, 2H), 1.48 (14-CH$_3$, d, 7 Hz, 3H).

EXAMPLE 11

Ethyl,[5,8,13,14-tetrahydro-14-methyl-8,13-dioxobenz[5,6]isoindolo[2,1-b]isoquinolin-12-yl]phosphoric acid, sodium salt Sodium iodide (2.0 g) was added to a solution of Intermediate 10(a) (2.0 g) in acetone (100 ml) and the mixture was heated under reflux for 5 h. After this time, a second portion of sodium iodide (2.0 g) was added and the reaction mixture was maintained under reflux for 16 h. The reaction mixture was cooled to 20° and the precipitated product was collected by filtration, washed with acetone (2×20 ml) and dried to give a green solid (1.75 g). Crystallisation of this solid (1.75 g) from a mixture of water (20 ml) and acetone (800 ml) gave the title compound as a green solid (1.125 g); $\lambda_{max}$ 243.6 nm, $E_1^1$ 973, 367.2 nm, $E_1^1$ 173; δ (d$_6$-DMSO) 5.41 (5-H, d, 16 Hz, 1H), 5.31 (5-H, d, 16 Hz, 1H), 4.87 (14-H, q, 7 Hz, 1H), 3.88 (OCH$_2$CH$_3$, m, 2H), 1.45 (14-CH$_3$, d, 7 Hz, 3H), 1.10 (OCH$_2$CH$_3$, t, 6 Hz, 3H).

EXAMPLE 12

2-Methoxyethyl,[5,8,13,14-tetrahydro-14-methyl-8,13-dioxobenz[5,6]isoindolo[2,1-b]isoquinolin-9-yl]phosphoric acid, sodium salt Sodium iodide (0.637 g) was added to a solution of Intermediate 4(j) (2.03 g) in acetone (40 ml). The resulting solution was refluxed for 3 h and more sodium iodide (1.274 g) was added. Refluxing was continued for 20 h. The reaction mixture was evaporated and the residue was redissolved in 2-butanone (40 ml). The resulting solution was refluxed for 2 h and then evaporated. The residue was triturated with ether (3×25 ml) to give a solid. Water (200 ml) was added and the resulting suspension was acidified to pH 1.5 with 2M hydrochloric acid and extractred with dichloromethane (3×300 ml). Salt solution was added during the extraction to disperse an emulsion. The organic extracts were dried over anhydrous sodium sulphate and evaporated to a solid. This solid was suspended in water (200 ml) and 0.1M sodium hydroxide solution was added to pH 7.0. The mixture was filtered and the filtrate was freeze-dried to a foam. Treatment of the foam with acetone (120 ml) gave a solution which was filtered and evaporated. The residue was triturated with ether (40 ml) to give the title compound as a yellow solid (1.34 g); $\lambda_{max}$ 244.0 nm, $E_1^1$ 1034, 366.8 nm, $E_1^1$ 208; δ (d$_6$-DMSO) 5.40 (5-H, d, 17 Hz, 1H), 5.30 (5-H, d, 17 Hz, 1H), 4.80 (14-H, q, 7 Hz, 1H), 3.96 (POCH$_2$, m, 2H), 3.44 (POCH$_2$CH$_2$, q, 5 Hz, 2H), 3.22 (OCH$_3$, s, 3H), 1.47 (14-CH$_3$, d, 7 Hz, 3H).

EXAMPLE 13

Propyl,[5,8,13,14-tetrahydro-14-methyl-8,13-dioxobenz[5,6]isoindolo[2,1-b]isoquinolin-9,12-diyl]phosphoric acid, sodium salt Sodium iodide (2.5 g) was added to as solution of Intermediate 12 in butan-2-one (50 ml) and the reaction mixture was stirred under reflux for 4 h and evaporated to dryness. The residue was dissolved in methanol and chromatographed on Sephadex LH 20 in methanol twice to give title compound as a dark yellow solid (595 mg), $\lambda_{max}$ (water) 244.8 nm, $E_1^1$ 637, 356.4 nm, $E_1^1$ 140; δ (DMSO) 5.28+5.38 (5H), 4.82 (14H), 3.65–3.85 (CH$_2$), 1.35–1.6 (14CH$_3$+CH$_2$), 0.70–0.90CH$_3$.

EXAMPLE 14

4-Nitrophenylmethyl,[5,8,13,14-tetrahydro-14-methyl-8,13-dioxobenz[5,6]isoindolo[2,1-b]isoquinolin-9-yl]phosphoric acid, triethylamine salt Triethylamine hydroiodide (278 mg) was added to a solution of Intermeidate 5(b) (750 mg) in acetone (75 ml). The resulting solution was refluxed for 4 h. Further triethylamine hydroiodide (278 mg) was added and refluxing continued for a further 17 h. The reaction mixture was evaporated and the residual oil was washed with ether. The oil was dissolved in water (100 ml) and extracted with dichloromethane (2×100 ml) then with dichloromethane-methanol (1:1, 100 ml) then with dichloromethane (100 ml). The combined organic extracts were dried over anhydrous sodium sulphate and evaporated. Water (250 ml) was added to the residue and the resulting solution was filtered and freeze-dried to a foam. This foam was dissolved in water (50 ml) and the solution filtered. The filtrate was acidified to pH 1.5 with 2M hydrochloric acid and extracted with dichloromethane-methanol (2:1, 450 ml) then with dichloromethane (100 ml). The combined organic extracts were washed with water and dried over anhydrous sodium sulphate. Triethylamine (0.1 ml, 0.7 g) was added and the solution was evaporated. The residual oil was dissolved in water (30 ml), the solution was filtered and the filtrate was freeze-dried to give the title compound as a yellow foam (256 mg); $\lambda_{max}$ 244.2 nm, $E_1^1$ 739, 365.8 nm, $E_1^1$ 129; δ (d$_6$-DMSO) 5.39 (5-H, d, 17 Hz, 1H), 5.29 (5-H, d, 17 Hz, 1H), 5.10 (POCH$_2$, d, 8 Hz, 2H), 4.80 (14-H, q, 7 Hz, 1H), 2.98–3.13 (N$^+$—CH$_2$CH$_3$, m, 6H), 1.47 (14-CH$_3$, d, 7 Hz, 3H), 1.18 (N$^+$—CH$_2$CH$_3$, t, 7 Hz, 9H).

EXAMPLE 15

Phenylmethyl,[5,8,13,14-tetrahydro-14-methyl-8,13-dioxobenz[5,6]isoindolo[2,1-b]isoquinolin-9-yl]phosphoric acid Sodium iodide (285 mg) was added to a solution of Intermediate 5(a) (1.019 g) in acetone (25 ml) and the mixture was heated under reflux. After 1.5 h, the reaction mixture was evaporated to dryness and the residue was diluted with water (100 ml), acidified to pH 2 to 3 with 2M-hydrochloric acid and extracted with dichloromethane (3×100 ml). Salt solution was added during the extraction procedure to disperse the emulsion which was formed. The combined organic extracts were dried over anhydrous sodium sulphate and evaporated to a green oil which solidifed. The solid was stirred in ether (50 ml) for 10 min. and then collected by filtration to give a green solid. Crystallisation of the solid from a mixture of chloroform (containing a trace of ethanol) and ether gave the title compound as green crystals (427 mg); $\lambda_{max}$ 245.0 nm, $E_1^1$ 979, 369.0 nm, $E_1^1$ 193; δ (d$_6$-DMSO) 5.44 (5-H, d, 16 Hz, 1H), 5.36 (5H, d, 16 Hz, 1H), 5.23 (OCH$_2$, d, 8 Hz, 2H), 4.86 (14-H, q, 7 Hz, 1H), 1.51 (14-CH$_3$, d, 7 Hz, 3H).

EXAMPLE 16

Phenylmethyl,[5,8,13,14-tetrahydro-14-methyl-8,13-dioxobenz[5,6]isoindolo[2,1-b]isoquinolin-9-yl]phosphoric acid, sodium salt A solution of sodium 2-ethylhexanoate (1.55 g) in tetrahydrofuran (14 ml) was added over 2 min to a stirred suspension of the product of Example 15 (4 g) under nitrogen. Water (0.4 ml) was added to the resulting clear solution which was then diluted with propan-2-ol (215 ml) over 40 min. The resulting suspension was stirred for 20 min and the solid was collected by filtration, washed with propan-2-ol (3×30 ml), sucked dry under nitrogen and dried in vacuo to give the title compound as a yellow-green amorphous solid (3.19 g); $\lambda_{max}$ 244 nm (MeOH), $E_1^1$ 843, having a similar $^1$H N.m.r. spectrum to the sample obtained in Example 2(a).

EXAMPLE 17

Phenylmethyl,[5,8,13,14-tetrahydro-14-methyl-8,13-dioxobenz[5,6]isoindolo[2,1-b]isoquinolin-9-yl]phosphoric acid, potassium salt Potassium iodide (1.83 g) was added to a suspension of Intermediate 5(a) (5.90 g) in a mixture of acetone (118 ml) and water (2.93 ml). This mixture was stirred and heated to reflux under nitrogen for 2.5 h, a crystalline precipitate forming after 40 min. The suspension was cooled to 21° and stirred for 1 h and the solid was collected by filtration, washed with acetone (2×25 ml) and dried in vacuo to give the title compound (4.32 g); $\lambda_{max}$ 244 nm (MeOH), $E_1^1$ 813; δ (d$_6$-DMSO) 5.36 (5-H, d, 16 Hz, 1H), 5.24 (5-H, d, 16 Hz, 1H), 4.96 (OCH$_2$, d, 6 Hz, 2H), 4.80 (14-H, q, 7 Hz, 1H), 1.48 (14-CH$_3$, d, 7 Hz, 3H).

EXAMPLE 18

Phenylmethyl,[5,8,13,14-tetrahydro-14-methyl-8,13-dioxobenz[5,6]isoindolo[2,1-b]isoquinolin-9-yl]phosphoric acid, lithium salt Lithium iodide trihydrate (1.88 g) was added to a suspension of Intermediate 5(a) (5.90 g) in a mixture of acetone (118 ml) and water (2.3 ml). This mixture was stirred and heated to reflux under nitrogen for 2.7 h, a crystalline precipitate forming after 20 min. The suspension was cooled to ca. 20° and stirred for 2 h and the solid was collected by filtration, washed with acetone (3×50 ml) and dried in vacuo at 20° to give the title compound (4.72 g); $\lambda_{max}$ 244 nm (MeOH), $E_1^1$ 847; δ (d$_6$-DMSO) 5.43 (5-H, d, 16 Hz, 1H), 5.31 (5-H, d, 16 Hz, 1H), 5.04 (OCH$_2$, d, 6 Hz, 2H), 4.84 (14-H, q, 7 Hz, 1H), 1.49 (14-CH$_3$, d, 7 Hz, 3H)

EXAMPLE 19

Phenylmethyl,[5,8,13,14-tetrahydro-14-methyl-8,13-dioxobenz[5,6]isoindolo[2,1-b]isoquinolin-9-yl]phosphoric acid, L-arginine salt A suspension of the product of Example 15 (2 g) in water (80 ml) was stirred under nitrogen and a solution of L-arginine monohydrate (0.70 g) in water (10 ml) was added dropwise over 15 min to adjust the pH to 6.1. The pH was raised to 7.0 by the addition of part (2 ml) of a solution of L-arginine (0.1 g) in water (5 ml), and the resulting clear solution was filtered. the filtrate was freeze-dried to give the title compound as a yellow-green solid (2.61 g); $\lambda_{max}$ 244 nm (MeOH), $E_1^1$ 648; δ (d$_6$-DMSO) 5.41 (5-H, d, 16 Hz, 1H), 5.29 (5-H, d, 16 Hz, 1H), 5.02 (OCH$_2$, d, 6 Hz, 2H), 4.83 (14-H, q, 7 Hz, 1H), 3.14 (NCH$_2$, $_t$, 6 Hz, 2H), 1.50 (14-CH$_3$, d, 7 Hz, 3H).

EXAMPLE 20

Phenylmethyl,[5,8,13,14-tetrahydro-14-methyl-8,13-dioxobenz[5,6]isoindolo[2,1-b]isoquinolin-9-yl]phosphoric acid, sodium salt (a) Sodium iodide (5.94 g) was added to a suspension of Intermediate 5(a) (21.2 g) in acetone (420 ml). This mixture was stirred and heated to reflux under nitrogen for 1.5 h, and the resulting solution was cooled to ca 35° and filtered. The filtrate was concentrated in vacuo to ca 50 ml, and the residue was stirred while diisopropyl ether (350 ml) was added. The resulting suspension was stirred for 45 min, and the green solid was collected by filtration, washed with diisopropyl ether (2×100 ml) and dried in vacuo at 30°. Part (2.0 g) of this solid was supended in refluxing acetone (20 g) and water (2.0 ml) was added. The resulting solution was seeded and stirred under reflux for 5 min while crystallisation occurred. The mixture was cooled to ca 20° over 30 min and refrigerated overnight, and the solid was collected by filtration, washed with chilled acetone (2×5 ml) and dried in vacuo to give the title compound as crystals (1.77 g); $\lambda_{max}$ 244 nm (MeOH), $E_1^1$ 857; $\upsilon_{max}$ (Nujol mull) 1662 (C=O), 1250 and 1110 cm$^{-1}$ (phosphate); δ (d$_6$-DMSO) 5.41 (5-H, d, 16 Hz, 1H), 5.29 (5-H, d, 16 Hz, 1H), 4.96 (OCH$_2$, d, 6 Hz, 2H), 4.82 (14-H, q, 7 Hz, 1H), 1.49 (14-CH$_3$, d, 7 Hz, 3H).

(b) Sodium iodide (1.65 g) was added to a suspension of Intermediate 5(a) (5.90 g) in a mixture of acetone (118 ml) and water (2.93 ml). This mixture was stirred and heated to reflux under nitrogen for 2 h, a pale yellow crystalline precipitate forming after 0.8 h. The suspension was cooled to 21° and stirred for 1 h, and the solid was collected by filtration, washed with acetone (2×25 ml) and dried in vacuo to give the title compound as crystals (4.96 g); $\lambda_{max}$ 244 nm (MeOH) $E_1^1$ 842, having infrared and $^1$H N.m.r. spectrta similar to the sample obtained in Example 20(a).

The following are examples of pharmaceutical compositions according to the invention. The term 'Active Ingredient' as used hereinafter means a compound of the linvention and may be for example the compounds of Examples 2(a) or 8.

Example A-Dry Powder for Injection

|  | mg/vial |
|---|---|
| Active ingredient | equivalent to 100 mg acid |
| trisodium citrate | 8.8 |
| Citric acid | 0.2 |

Method 1

Blend the sterile ingredients until homogeneous. Fill aseptically into glass vials. Purge the headspace with nitrogen and close the vials using rubber closures and metal overseals.

Method 2

Dissolve the ingredients in water for injections B.P. Sterilise the solution by membrane filtration. Aseptically fill into freeze-drying vials and place suitable rubber freeze-drying closures in position. Freeze-dry, filling the vials with nitrogen at the end of the cycle. Fully insert the closures and apply metal overseals.

Constitution

Constitute with a suitable sterile vehicle, e.g. using water for injections or using a 5% w/v dextrose solution, as an injection (e.g. in a 10 ml volume) or an infusion (e.g. in a 100 ml volume).

Example B-Oral Tablet

|  | mg/tablet |
|---|---|
| Active Ingredient | equivalent to 250 mg acid |
| Microcrystalline cellulose | 231 |
| Sodium starch glycolate | 6 |
| Magnesium stearate | 2 |

Sieve the ingredients and blend until homogeneous. Compress with appropriate punches. The tablets may be covered with a thin polymer coat applied by the usual film coating techniques. A pigment may be included in the film coat.

We claim:

1. A compound having a formula (1)

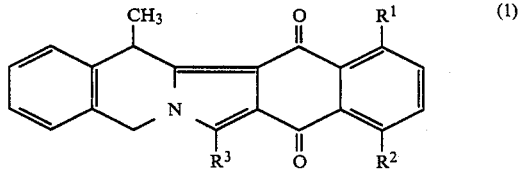

wherein $R^1$ and $R^2$, which may be the same or different, each represents a hydrogen atom, a hydroxyl group or a group $-OP(O)(OH)(OR^4)$, wherein $R^4$ represents a hydrogen atom or a straight-chain or branched $C_{1-8}$ alkyl (optionally substitued by a hydroxyl, $C_{1-4}$alkoxy, 3-7 membered cyclic ether, or $C_{3-7}$ cycloalkyl group), $C_{3-8}$ alkenyl, $C_{3-7}$ cycloalkyl, phenyl, phen $C_{1-3}$ alkyl or benzoyl $C_{1-3}$ alkyl group, wherein any phenyl moiety may optionally be substituted by a hydroxyl, $C_{1-4}$ alkoxy or nitro group, with the proviso that at least one of $R^1$ and $R^2$ represents a group $-OP(O)(OH)(OR^4)$; and $R^3$ represents a hydrogen of halogen atom or a methyl group; and salts thereof.

2. A compound of formula (1) as claimed in claim 1, wherein $R^1$ and $R^2$, which may be the same or different, each represents a hydrogen atom, a hydroxyl group or a group $-OP(O)(OH)(OR^4)$, where $R^4$ represents a hydrogen atom or a straight-chain or branched $C_{1-8}$ alkyl (optionally substituted by a hydroxyl, $C_{1-4}$ alkoxy, 3-7 membered cyclic ether, or $C_{3-7}$ cycloalkyl group), phenyl or phen $C_{1-3}$ alkyl, wherein any phenyl moiety may optionally be substituted by a hydroxyl, $C_{1-4}$ alkoxy or nitro group; and $R^3$ is a hydrogen or halogen atom or a methyl group; and salts thereof.

3. A compound of formula (1) as claimed in claim 1 wherein $R^4$ represents a straight chained $C_{1-5}$ alkyl group, a tetrahydrofuranylmethyl group, a phen $C_{1-3}$ alkyl group or a benzoyl $C_{1-3}$ alkyl group, and salts thereof.

4. A compound of formula (1) as claimed in claim 1 wherein $R^3$ represents a hydrogen atom, and salts thereof.

5. A compound of formula (1) as claimed in claim 1 wherein $R^1$ represents a hydrogen atom, and salts thereof.

6. A compound as claimed in claim 1 being phenylmethyl, [5,8,13,14-tetrahydro-14-methyl-8,13-dioxobenz[5,6]isoindolo[1,2-b]isoquinolin-9-yl]phosphoric acid, or 2-oxo-2-phenylethyl,[5,8,13,14-tetrahydro-14-methyl-8,13-dioxobenz[5,6]isoindolo[2,1-b]isoquinolin-9-yl]phosphoric acid, or a salt thereof.

7. A compound as claimed in claim 1 being the sodium salt of phenylmethyl, [5,8-tetrahydro-14-methyl-8,13-dioxobenz[5,6]-isoindolo[2,1-b]isoquinolin-9-yl]phosphoric acid.

8. A compound as claimed in claim 1 being the sodium salt 2-oxo-2-phenylethyl,[5,8,13,14-tetrahydro-14-methyl-8,13-dioxobenz[5,6]isoindolo[2,1-b]isoquinolin-9-yl]phosphoric acid.

9. A compound of formula (1) as defined in claim 4, wherein $R^1$ represents a hydrogen atom and salts thereof.

10. A compound of formula (2)

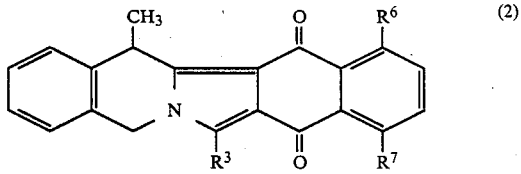

wherein $R^3$ represents a hydrogen or halogen atom or a methyl group; and one of $R^6$ and $R^7$ represents a group $-OP(O)(X^1)(X^2)$, where $X^1$ represents a halogen atom or a group $OX^3$, where $X^3$ represents a straight or branched $C_{1-8}$ alkyl group (optionally substituted by a hydroxyl, $C_{1-4}$ alkoxy, 3-7 membered cyclic ether or $C_{3-7}$ cycloalkyl group) or a $C_{3-8}$ alkenyl, $C_{3-7}$ cycloalkyl, phenyl, phen $C_{1-3}$ alkyl or benzoyl $C_{1-3}$ alkyl group, wherein any phenyl moiety may optionally be substituted by a hydroxyl, $C_{1-4}$ alkoxy or nitro group; $X^2$ represents a hydroxyl group or an $X^1$ moiety, and the other represents a hydrogen atom, hydroxyl group or a group $-OP(O)(X^1)(X^2)$; and salts thereof.

11. A pharmaceutical composition to combat cancers in a human or non-human animal body, comprising as an active ingredient an amount effective to combat cancers in a human or non-human animal body of a compound of formula (1) as defined in claim 1, or a physiologically acceptable salt thereof with one or more pharmaceutical carriers or excipients.

12. A method of treatment of the human or non-human animal body to combat cancers therein, which method comprises administering to the said body an effective amount of a compound of formula (1) of claim 1 or of a physiologically acceptable salt thereof.

* * * * *

UNITED STATES PATENT AND TRADEMARK OFFICE
CERTIFICATE OF CORRECTION

PATENT NO. :  4,851,399

DATED :  July 25, 1989

INVENTOR(S) :  Gordon H. PHILLIPPS et al

It is certified that error appears in the above-identified patent and that said Letters Patent is hereby corrected as shown below:

Col. 6, Claim 6, line 3, delete "[1,2-b]" and insert —[2,1-b]—.

Col. 6, Claim 7, line 2, delete "[5,8-" and insert — [5,8,13,14- —.

Signed and Sealed this

Twenty-first Day of August, 1990

Attest:

HARRY F. MANBECK, JR.

*Attesting Officer*         *Commissioner of Patents and Trademarks*